United States Patent [19]

Shimokawa

[11] Patent Number: 4,522,076
[45] Date of Patent: Jun. 11, 1985

[54] METHOD OF COLLECTING SAMPLES FROM MATERIAL ON A BELT CONVEYOR

[75] Inventor: Hiroshi Shimokawa, Kitakyushu, Japan

[73] Assignee: Kabushiki Kaisha Imamura Seisakusho, Kitaminato, Japan

[21] Appl. No.: 544,981

[22] Filed: Oct. 24, 1983

[30] Foreign Application Priority Data

Oct. 27, 1982 [JP] Japan ................... 57-187350

[51] Int. Cl.³ .............................................. G01N 1/20
[52] U.S. Cl. .............................. 73/863.41; 73/863.91
[58] Field of Search ........... 73/863.41, 863.43, 863.44, 73/863.51, 863.53, 863.54, 863.91, 863.92

[56] References Cited

U.S. PATENT DOCUMENTS

| | | | |
|---|---|---|---|
| 1,860,107 | 5/1932 | Lien | 73/863.51 |
| 3,302,769 | 2/1967 | Platzer | 73/863.41 |
| 3,688,587 | 9/1972 | Jirik | 73/863.53 |

FOREIGN PATENT DOCUMENTS 52-10795 1/1977 Japan ................... 73/863.44

Primary Examiner—S. Clement Swisher
Attorney, Agent, or Firm—Oldham, Oldham & Weber Co.

[57] ABSTRACT

A sample collecting method comprises advancing a baffle member to a position beneath the delivery end of an upstream main belt conveyor continuously conveying a material, advancing a collecting belt conveyor to a position beneath the baffle member, retracting the baffle member to permit transfer of a portion of the material from the main belt conveyor onto the collecting belt conveyor, advancing the baffle member again to terminate the transfer of the material from the main belt conveyor onto the collecting belt conveyor, stopping the collecting belt conveyor at the same time, and running the collecting belt conveyor in the opposite direction at low speed to collect as a sample an intermediate adequate portion of the mass of the material transferred onto the collecting belt conveyor.

5 Claims, 7 Drawing Figures

METHOD OF COLLECTING SAMPLES FROM MATERIAL ON A BELT CONVEYOR

BACKGROUND OF THE INVENTION

This invention relates to a method of collecting samples from a material, for example, coal or any other raw material being conveyed on a belt conveyor.

In the collection of a sample from such a material being conveyed on a belt conveyor, it is demanded to accurately collect a minimum required amount of the material covering the full width of the conveyor belt in a direction orthogonal with respect to the longitudinal direction of the conveyor belt. More precisely, referring to FIGS. 1a and 1b showing, in side elevation and plan respectively, a material 2 being conveyed on a belt conveyor 1, it is desired to accurately collect, as a sample, a limited portion 3 of the material 2 occupying a short length (FIG. 1a) in the longitudianl direction of the conveyor belt and covering the full width (FIG. 1b) in the transverse direction of the conveyor belt.

SUMMARY OF THE INVENTION

It is a primary object of the present invention to provide a novel method of sample collection which satisfies the demand above described.

The present invention resides in a method of collecting samples from a material on a belt conveyor comprising the steps of advancing a baffle member to a position beneath the delivery end of an upstream main belt conveyor continuously conveying a material, advancing a collecting belt conveyor to a position beneath said baffle member, retracting said baffle member to permit transfer of a portion of the material from said main belt conveyor onto said collecting belt conveyor running in the same direction as that of said main belt conveyor at the same speed as that of said main belt conveyor, advancing said baffle member to the position beneath said delivery end of said main belt conveyor again to terminate the transfer of the material from said main belt conveyor onto said collecting belt conveyor, stopping the operation of said collecting belt conveyor at the same time, and then running said collecting belt conveyor at low speed to collect as a sample a portion of the mass of the material transferred onto said collecting belt conveyor.

BRIEF DESCRIPTION OF THE DRAWINGS

FIG. 1b is a schematic plan view of FIG. 1a;

A preferred embodiment of the method of the present invention will now be described in detail with reference to FIGS. 2 to 6.

DESCRIPTION OF THE PREFERRED EMBODIMENT

Figure 1A:
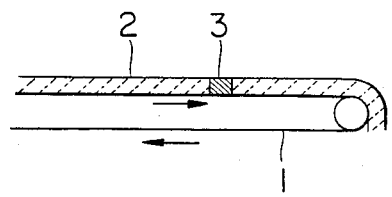
FIG. 1a is a schematic side elevation view of an upstream main belt conveyor and a material being conveyed thereon.
Figure 1B:
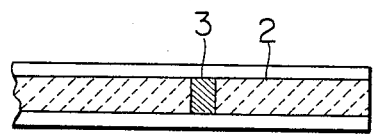
Figure 2:
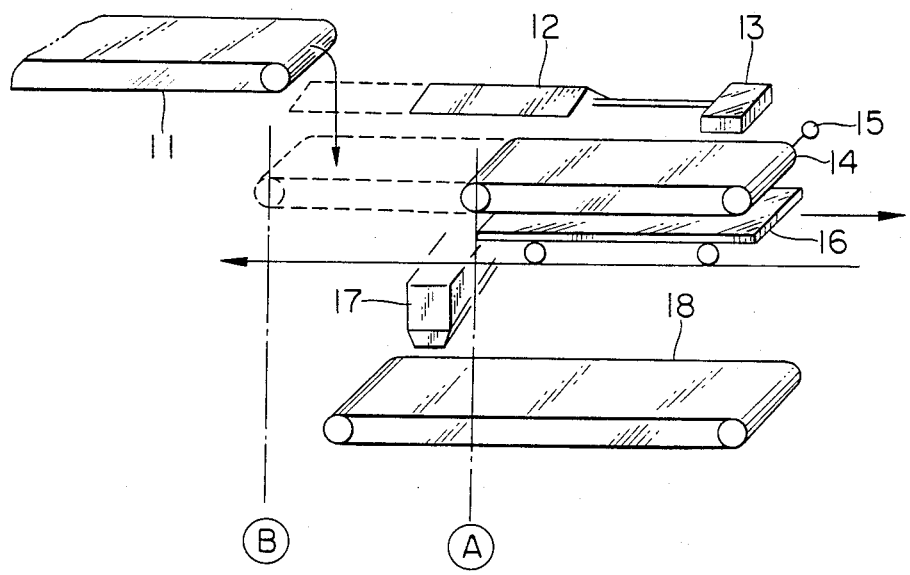
FIG. 2 is a schematic perspective view of a mechanism constructed for the practice of a preferred embodiment of the method of the present invention.

Referring to FIG. 2 which is a conceptional perspective view of a mechanism constructed for the practice of a preferred embodiment of the method of the present invention, a material being continuously conveyed rightward on an upstream main belt conveyor 11 shown on the left upper side of FIG. 2 falls, as shown by the solid arrow, from the right-hand delivery end of the upstream main belt conveyor 11 to be transferred onto a downstream main belt conveyor (not shown) disposed beneath the upstream main belt conveyor 11. The mechanism constructed for the practice of the method of the present invention is disposed between these upstream and downstream main belt conveyors.

The mechanism includes a baffle member 12 in the form of an angle bar of light weight disposed at a level lower than that of the right-hand delivery end of the upstream main belt conveyor 11. This baffle member 12 is coupled to a drive unit 13 so that it can be moved at high speed between an advanced position B directly beneath the delivery end of the upstream main belt conveyor 11 and a retracted position A spaced apart from the position B in the running direction of the upstream main belt conveyor 11.

A collecting belt conveyor 14 is disposed beneath the baffle member 12 and is mounted on a truck 16 whose movable direction and distance are the same as those of the baffle member 12. The width of the collecting belt conveyor 14 is substantially the same as that of the upstream main belt conveyor 11. The running speed of the collecting belt conveyor 14 is at least as high as that of the main belt conveyor 11 when it runs in the same direction, but it runs at low speed in the opposite direction.

A chute 17 is disposed directly beneath the retracted position A of the left-hand end of the collecting belt conveyor 14, and a sample-receiving belt conveyor 18 is sisposed beneath the chute 17.

A pulse generator 15 is associated with the collecting belt conveyor 14 so that the run distance of the belt of the collecting belt conveyor 14 can be measured.

The truck 16, the collecting belt conveyor 14 and the baffle member 12 constitute a unit which is called herein a sampler with baffle (which will be abbreviated hereinafter as a sampler).

Normally, the sampler stands by at the retracted position A in which the baffle member 12 is retracted. Therefore, in this position of the sampler, the entirety of the material being continuously conveyed on the upstream main belt conveyor 11 falls from the righthand delivery end of the upstream main belt conveyor 11 onto the downstream main belt conveyor (not shown), and even a portion of the material does not fall onto the collecting belt conveyor 14.

Figure 3:
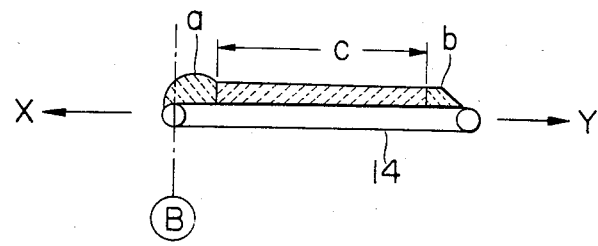
FIGS. 3 to 5 are schematic side elevation views showing different states of a material on the collecting belt conveyor shown in FIG. 2.
Figure 4:
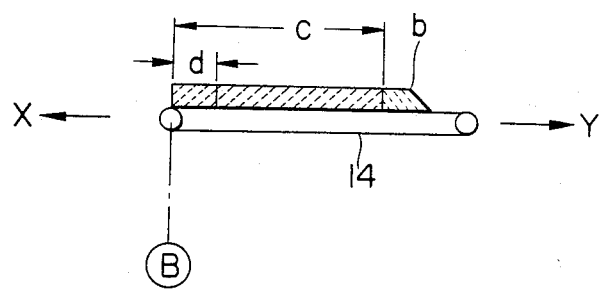
Figure 5:
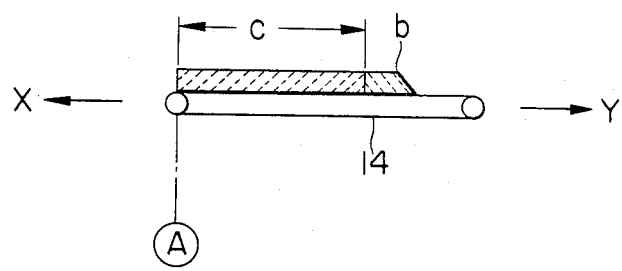
Figure 6:
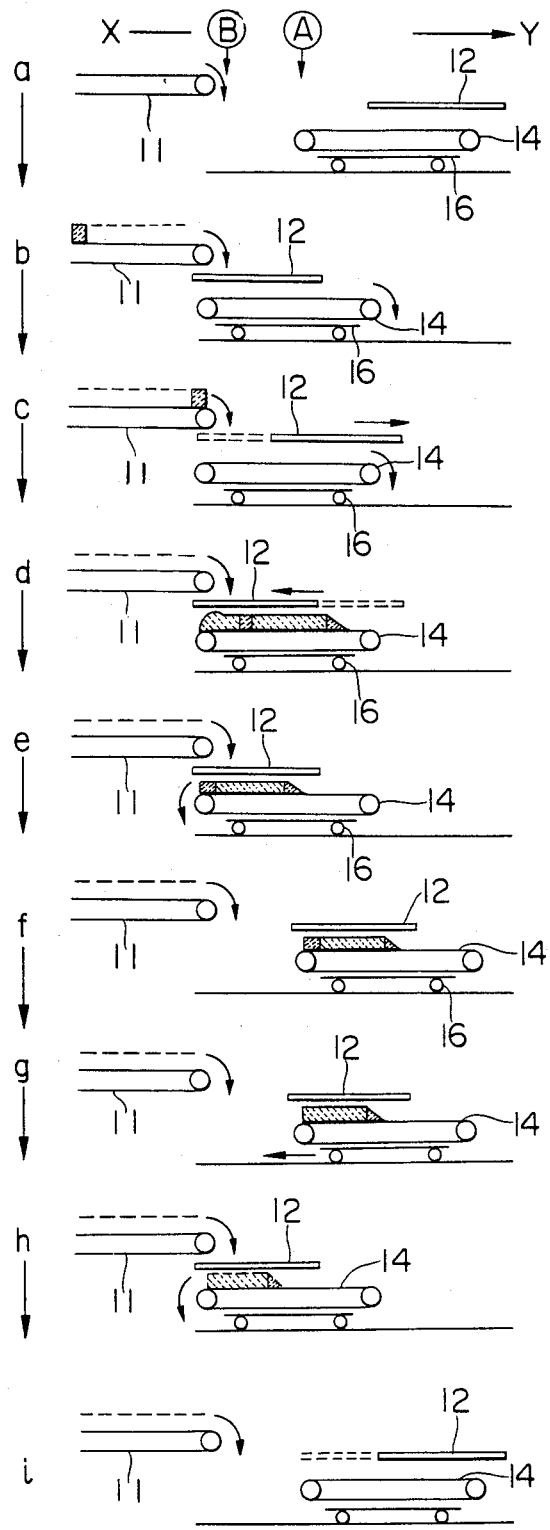
FIG. 6 shows schematically in (a) to (i) the steps of sample collection according to the method of the present invention.

Sample collection by the mechanism shown in FIG. 2 will be described in detail with reference to FIGS. 2 and 6 and also with reference to FIGS. 3 to 5.

When sample collection is commanded from a command unit (not shown) in the stand-by condition shown in FIG. 6(a), the upper run of the belt of the collecting belt conveyor 14 is driven at high speed in a direction as shown by the arrow Y or rightward in FIG. 6(a). The running speed of the belt of the collecting belt conveyor 14 is the same as that of the upstream main belt conveyor 11, and the running direction of the former is also the same as that of the latter.

When the sample collecting condition is reached, the baffle member 12 is moved by the drive unit 13 in a direction as shown by the arrow X or leftward in FIG. 6(a) until it is fully advanced to the position B where the baffle member 12 baffles the flow of the material falling from the delivery end of the upstream main belt conveyor 11, as shown in FIG. 6(b). That is, the baffle member 12 baffles the flow of the falling material so that the material may not fall onto the sampler or the collecting belt conveyor 14 (running at high speed already) mounted on the truck 16 having been moved to the position B simultaneously with the leftward movement of the baffle member 12. Therefore, the material is smoothly transferred from the upstream main belt conveyor 11 onto the downstream main belt conveyor (not shown) while being guided along the baffle member 12.

Then, under command of the command unit, the baffle member 12 is moved at high speed in the direction of the arrow Y until it is retracted to and stopped at a position where a portion of the material being conveyed on the upstream main belt conveyor 11 can be sufficiently transferred onto the collecting belt conveyor 14. Thus, a suitable amount of the material falling from the delivery end of the upstream main belt conveyor 11 running at high speed is collected on the collecting belt conveyor 14 running at the same high speed. The amount of the collected portion of the material is such that the material does not spill out from the edges of the collecting belt conveyor 14. As soon as the material in an amount not exceeding the spill-out limit is collected on the collecting belt conveyor 14, the operation of the belt of the collecting belt conveyor 14 is stopped, and the baffle member 12 is moved in the direction of the arrow X again at high speed as shown in FIG. 6(d) to function so that any extra amount of the material may not fall onto the collecting belt conveyor 14. The state of the mass of the material thus transferred onto the collecting belt conveyor 14 is the same as that of the material having been conveyed on the upstream main belt conveyor 11 as far as the width is concerned. However, the leading and trailing end portions b and a of the mass of the collected material are not adequate in shape or contour as seen in FIGS. 3 and 6(d). It is therefore desirable to extract a sample from the intermediate adequate portion c of the mass of the collected material.

To this end, the belt of the collecting belt conveyor 14 is run in the direction of the arrow X at low speed while maintaining the baffle member 12 in the position overlying the collecting belt conveyor 14 as shown in FIG. 6(e), so as to discharge the portion a of the mass of the collected material from the collecting belt conveyor 14 onto the downstream main belt conveyor. After the removal of the portion a of the mass of the collected material, the operation of the belt of the collecting belt conveyor 14 is stopped again. This stopping timing is determined by a pulse signal generated from the pulse generator 15 associated with the collecting belt conveyor 14. FIG. 4 shows the state of the mass of the material remaining on the collecting belt conveyor 14 after the stop shown in FIG. 6(e).

Then, the sampler is retracted in the direction of the arrow Y toward the position A as shown in FIG. 6(f). The sampler is stopped at the position A where the left-hand delivery end of the collecting belt conveyor 14 registeres with the chute 17 shown in FIG. 2. The belt of the collecting belt conveyor 14 is then run in the direction of the arrow X at low speed to cause falling of a sample d of an adequate or predetermined amount into the chute 17. As soon as the sample d has been transferred onto the sample-receiving belt conveyor 18 through the chute 17, the operation of the belt of the collecting belt conveyor 14 is stopped in response to a stop signal FIGS. 6(g) and 5 show the state of the sampler and the state of the remaining mass of the material on the collecting belt conveyor 14 after the transfer of the sample d onto the sample-receiving belt conveyor 18. This stop signal is also provided by a pulse signal generated from the pulse generator 15 associated with the collecting belt conveyor 14.

The sampler is then moved or advanced in the direction of the arrow X until it is stopped at the position B. The belt of the collecting belt conveyor 14 is run in the direction of the arrow X so as to discharge the entirety of the remaining mass of the collected material from the collecting belt conveyor 14 onto the downstream main belt conveyor, as shown in FIG. 6(h). After complete discharge of the remaining mass of the collected material, the operation of the belt of the collecting belt conveyor 14 is stopped, and the sampler is retracted to the position A which is the initial stand-by position, as shown in FIG. 6(i).

It will thus be seen that, from a material being continuously conveyed on the upstream main belt conveyor 11, a portion occupying the full width of the belt and covering a predetermined region on the belt can be accurately extracted as a sample. In other words, a best sample can be collected from a material being conveyed on the main belt conveyor 11. Further, the final amount of the collected sample can be changed as desired.

According to the method of the present invention, the truck 16 need not be driven at a variable speed thereby permitting simple control of the sampler, and the structure of the sampler is also simplified.

Although one of the ends of the material collected on the collecting belt conveyor 14 is schematically illustrated by a vertical line in FIGS. 3 to 6, it is needless to mention that such an end has actually a natural angle of repose.

What is claimed is:

1. A method of collecting samples from a material on a belt conveyor comprising the steps of advancing a baffle member to a position beneath the delivery end of an upstream main belt conveyor continuously conveying a material, advancing a collecting belt conveyor to a position beneath said baffle member, retracting said baffle member to permit transfer of a portion of the material from said main belt conveyor onto said collecting belt conveyor running in the same direction as that of said main belt conveyor at the same speed as that of said main belt conveyor, advancing said baffle member to the position beneath said delivery end of said main belt conveyor again to terminate the transfer of the material from said main belt conveyor onto said collecting belt conveyor, stopping the operation of said collecting belt conveyor at the same time, and then running said collecting belt conveyor at low speed to collect as a sample a portion of the mass of the material transferred onto said collecting belt conveyor.

2. A sample collecting method as claimed in claim 1, wherein said collecting belt conveyor is carried by a truck capable of making advancing and retracting movement in a direction parallel to an extension of said upstream main belt conveyor.

3. A sample collecting method as claimed in claim 1 or 2, wherein, after the transfer of the material onto said collecting belt conveyor from said upstream main belt conveyor, said collecting belt conveyor is run once at low speed to remove an end portion of the mass of the material collected on said collecting belt conveyor, the operation of said collecting belt conveyor being then stopped, and, subsequently, said collecting belt conveyor is run again at low speed for sampling as said sample a predetermined amount of an intermediate adequate portion of the mass of the material collected on said collecting belt conveyor.

4. A sample collecting method as claimed in claim 3, wherein the running direction of said collecting belt conveyor running at low speed is opposite to the running direction of said upstream main belt conveyor, and said sample is transferred from said collecting belt conveyor onto a sample-receiving belt conveyor through a chute disposed beneath the end of said collecting belt conveyor which is nearer to said upstream main belt conveyor.

5. A sample collecting method as claimed in claim 4, wherein said end portion of the mass of the material collected on said collecting belt conveyor is removed while said collecting belt conveyor is situated beneath said delivery end of said upstream main belt conveyor, and said collecting belt conveyor is then retracted together with said truck to its retracted position where said sample is transferred from said collecting belt conveyor onto said sample-receiving belt conveyor.

* * * * *